(12) United States Patent
Westner et al.

(10) Patent No.: US 8,789,407 B2
(45) Date of Patent: Jul. 29, 2014

(54) METHOD AND MEASURING DEVICE FOR DETERMINING THE CONTENT IN AT LEAST ONE FILTER AID IN A LIQUID MEDIUM

(75) Inventors: Hans Westner, Hochstätten (DE); Thomas Stienen, Unna (DE)

(73) Assignee: KHS GmbH, Dortmund (DE)

( * ) Notice: Subject to any disclaimer, the term of this patent is extended or adjusted under 35 U.S.C. 154(b) by 358 days.

(21) Appl. No.: 12/935,126

(22) PCT Filed: Mar. 21, 2009

(86) PCT No.: PCT/EP2009/002100
§ 371 (c)(1),
(2), (4) Date: Sep. 28, 2010

(87) PCT Pub. No.: WO2009/124649
PCT Pub. Date: Oct. 15, 2009

(65) Prior Publication Data
US 2011/0023588 A1    Feb. 3, 2011

(30) Foreign Application Priority Data
Apr. 9, 2008 (DE) .......................... 10 2008 018 102

(51) Int. Cl.
*G01N 15/04* (2006.01)
(52) U.S. Cl.
USPC ......................................................... 73/61.63
(58) Field of Classification Search
USPC .................................. 210/777, 778; 73/61.63
See application file for complete search history.

(56) References Cited

U.S. PATENT DOCUMENTS

| | | | | |
|---|---|---|---|---|
| 3,677,406 A * | 7/1972 | King et al. | ..................... | 210/740 |
| 3,693,797 A * | 9/1972 | Topol | ........................... | 210/96.1 |
| 4,118,778 A * | 10/1978 | Strub | .............................. | 700/271 |
| 4,151,080 A * | 4/1979 | Zuckerman et al. | .......... | 210/741 |
| 4,514,306 A * | 4/1985 | Pato | ............................... | 210/740 |
| 5,772,867 A * | 6/1998 | Chiang et al. | ................... | 210/90 |
| 6,589,430 B1 * | 7/2003 | Pecar et al. | ................... | 210/741 |
| 2003/0116508 A1 | 6/2003 | Ballreich et al. | | |
| 2006/0073077 A1 | 4/2006 | Centanni | | |

FOREIGN PATENT DOCUMENTS

| | | |
|---|---|---|
| CH | 503 319 A | 2/1971 |
| DE | 276239 | 7/1914 |
| DE | 2054232 | 5/1972 |
| DE | 3514958 | 10/1986 |
| DE | 195 40 456 | 5/1997 |
| DE | 196 12 313 | 10/1997 |
| DE | 19751180 | 2/1999 |
| DE | 19963421 | 7/2001 |

OTHER PUBLICATIONS

International Preliminary Report on Patentability received in International Application No. PCT/EP2009/002100 dated Nov. 18, 2010.

* cited by examiner

*Primary Examiner* — Hezron E Williams
*Assistant Examiner* — Nathaniel Kolb
(74) *Attorney, Agent, or Firm* — Occhiuti & Rohlicek LLP

(57) ABSTRACT

The invention relates to a novel method for determining or measuring the content of at least one filter aid in an un-filtered product.

21 Claims, 3 Drawing Sheets

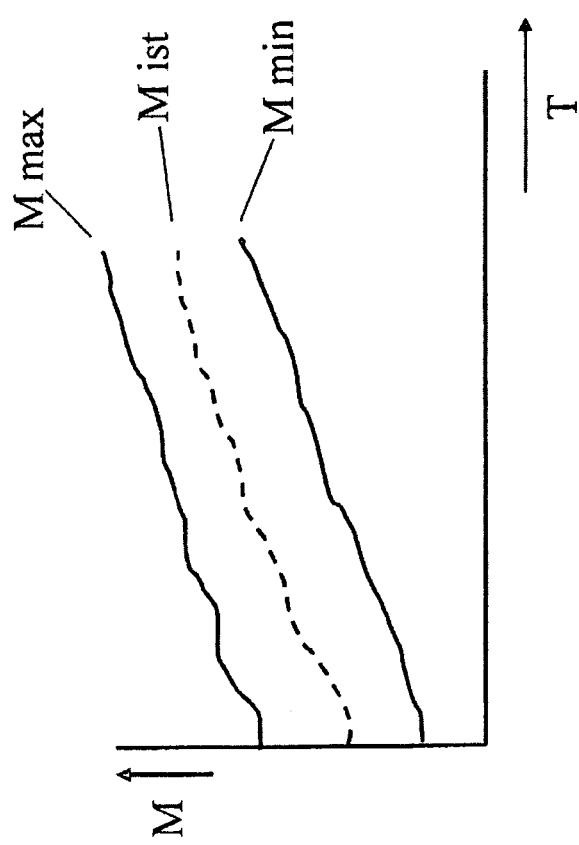

METHOD AND MEASURING DEVICE FOR DETERMINING THE CONTENT IN AT LEAST ONE FILTER AID IN A LIQUID MEDIUM

CROSS-REFERENCE TO RELATED APPLICATIONS

This application is the National Stage of International Application No. PCT/EP2009/002100 filed on Mar. 21, 2009, which claims the benefit of the priority date of German Patent Application No. 10 2008 018 102.1, filed on Apr. 9, 2008. The contents of both applications are hereby incorporated by reference in their entirety.

FIELD OF INVENTION

The invention relates to a method and a device for determining the content of at least one filter aid in a liquid medium, for example in an unfiltered product.

BACKGROUND

In the case of the filtration of liquid media or liquids, for example in the case of the filtration of beverages, e.g. beer, as a rule, filters, e.g. tank filters also, with filter cartridges are used, the filters making necessary the addition of a filter aid, e.g. diatomite, in order to obtain the desired filtration result.

The filter aid, which is mixed with the unfiltered product, is deposited on a filter element that separates an unfiltered space from a filtered space, for example on the outside of the filter cartridge, and there forms a filter layer, which accommodates the substances to be filtered out of the unfiltered product, such as sludge.

For an optimum filtration result it is necessary to add a certain quantity of filter aid to the medium or product to be filtered per unit (quantity, weight or volume). In this case it must be kept in mind that through the geometric dimension of the respective filter, for example through the geometric dimension of the tank filter, the filter cartridge, the space between each of the filter cartridges, etc., only a certain maximum quantity of filter aid can be accommodated in the relevant filter. Once this maximum quantity has been reached, the relevant filter has to be cleaned and/or back-flushed which causes interruption to the normal production.

In order, on the one hand, to obtain the optimum filtration result and, on the other hand, to keep the times between two cleaning and back-flushing operations as great as possible, attempts are made to meter the addition or the admixing of the filter aid to the medium or unfiltered product to be filtered in as precise a manner as possible. Up to now, in particular, this has not been possible in an automated manner or has only been possible with very unsatisfactory results.

Normally the filter aid is supplied to the unfiltered product as a suspension, which contains the filter aid in a liquid, for example in water or in the medium to be filtered. The production of the suspension is then effected, for example, by means of an agitator, by means of which the filter aid is mixed with the liquid and is slurried to form a suspension.

In the case of known methods for creating the suspension, however, continuous manual interventions are necessary on the part of the operating personnel and this, among other things, leads to the composition of the suspension, i.e. the proportion of the filter aid in the suspension, not being known with the necessary amount of precision. The result of this is that a simple quantity-controlled and/or volume-controlled adding of the suspension to the medium or unfiltered product to be filtered does not result in the filter aid being metered with a sufficient degree of precision.

To this must be added that the metering pumps normally used for adding the suspension have considerable inaccuracies, such that, when seen overall, automated metering of the filter aid has not been possible up to now with a satisfactory degree of precision.

In addition, it is known to investigate the filtrate flow, i.e. the liquid medium after the filtration, for the presence of slurry, for example also for the presence of filter aid, for example by using a scattered light turbidity measurement or by an absorption measurement. Using these known methods it is possible in a rough manner to determine or indicate changes in concentration, among other things, of the filter aid in the filtrate, in no way, however, is it possible to determine and/or indicate the actual content of the filter aid in the filtrate. Using the known methods neither is it possible, in particular, to determine the quantity of the filter aid supplied to the unfiltered product and consequently to the respective filter, nor to control, regulate or define it in an automated manner. In this case, in particular, the determining of the total quantity of the filter aid supplied to a filter is important as each filter can only accommodate a certain quantity of filter aids, and as exceeding the quantity, so-called overloading the filter, as a rule results in damaging the filter.

SUMMARY

It is the object of the invention to provide a method by way of which the determining or measuring of the content of the at least one filter aid in a liquid medium or unfiltered product is possible with a high degree of precision. Through the use of at least two measuring points, which are located spatially spaced apart and each of which supplies a measured value that corresponds to at least one chemical and/or physical characteristic of the liquid medium that changes with the presence of the at least one filter aid, very precise determining of the content or the proportion of the at least one filter aid in the liquid medium is possible by comparing the measured values of the measuring points, in particular also by the fact that influencing variables that influence or falsify the respective measured value, including those of the liquid medium or changes to such influencing variables are compensated by the use of at least two measured values.

These types of influencing variables, not caused by the presence or lack of filter aid, are, for example, the temperature, the time available for the respective measurement, the proportion of undissolved or out-gassed $CO_2$ in the liquid medium, etc. and the changes in the influencing variables.

The chemical and/or physical characteristics determined from the measuring point can be of the most varied type with corresponding design and adaptation of the measuring points, for example but not in a restricting manner, electric characteristics of the liquid medium, such as conductivity, capacity, mechanical and flow characteristics of the liquid medium, such as density, viscosity, pressure, back pressure, absolute pressure, differential pressure, also pressure drop at a flow restrictor, visual characteristics of the liquid medium, such as reflection capacity, transparency, chemical characteristics of the liquid medium, such as pH value, etc. The measuring points are correspondingly adapted for measuring the characteristics.

To increase the precision, it can be expedient for at least one of the measuring points, preferably however all the measuring points, to be realized for determining different chemical and/or physical characteristics, the measured values corresponding to the characteristics then being provided either in each case in parallel, i.e. at the same time or substantially at the same time, or serially, i.e. chronologically.

Further developments, advantages and applications of the invention proceed from both the subsequent description of exemplary embodiments and from the Figures. In this case, all features described and/or graphically represented are, in principle, individually or in arbitrary combination, objects of the invention, irrespective of their summary in the claims or their dependency. The content of the claims is also made a component of the description.

DESCRIPTION OF THE FIGURES

The invention is explained below by way of the Figures of one exemplary embodiment, in which, in detail:

FIG. 3 shows a schematic representation of the time development of a measurement value M at one of the measuring points of the measuring device in FIGS. 1 and 2.

DETAILED DESCRIPTION

Figure 1:
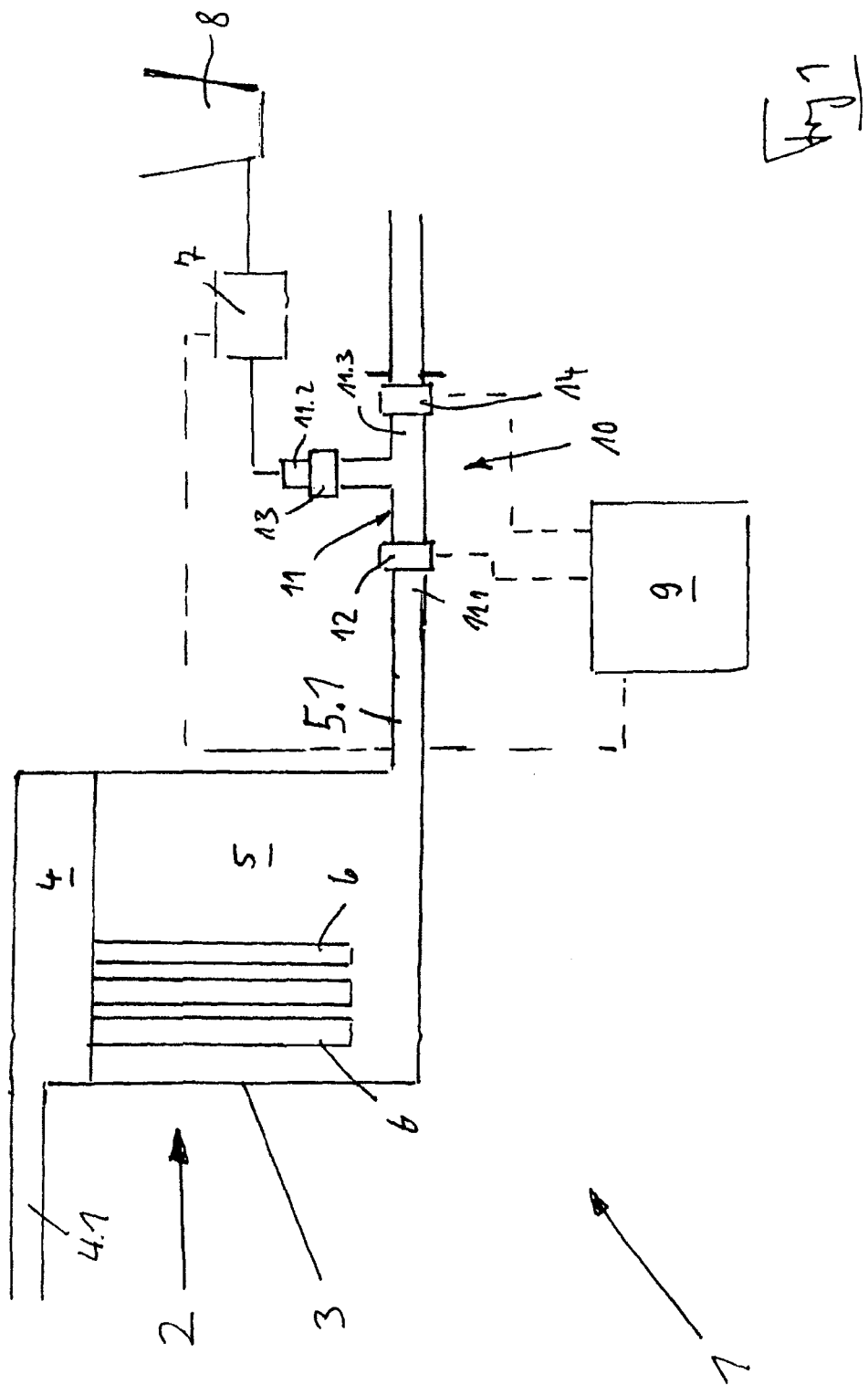
FIG. 1 shows a system for filtering liquid media, for example for filtering beverages, for example beer, together with a device for the metered addition of a filter aid.
Figure 2:
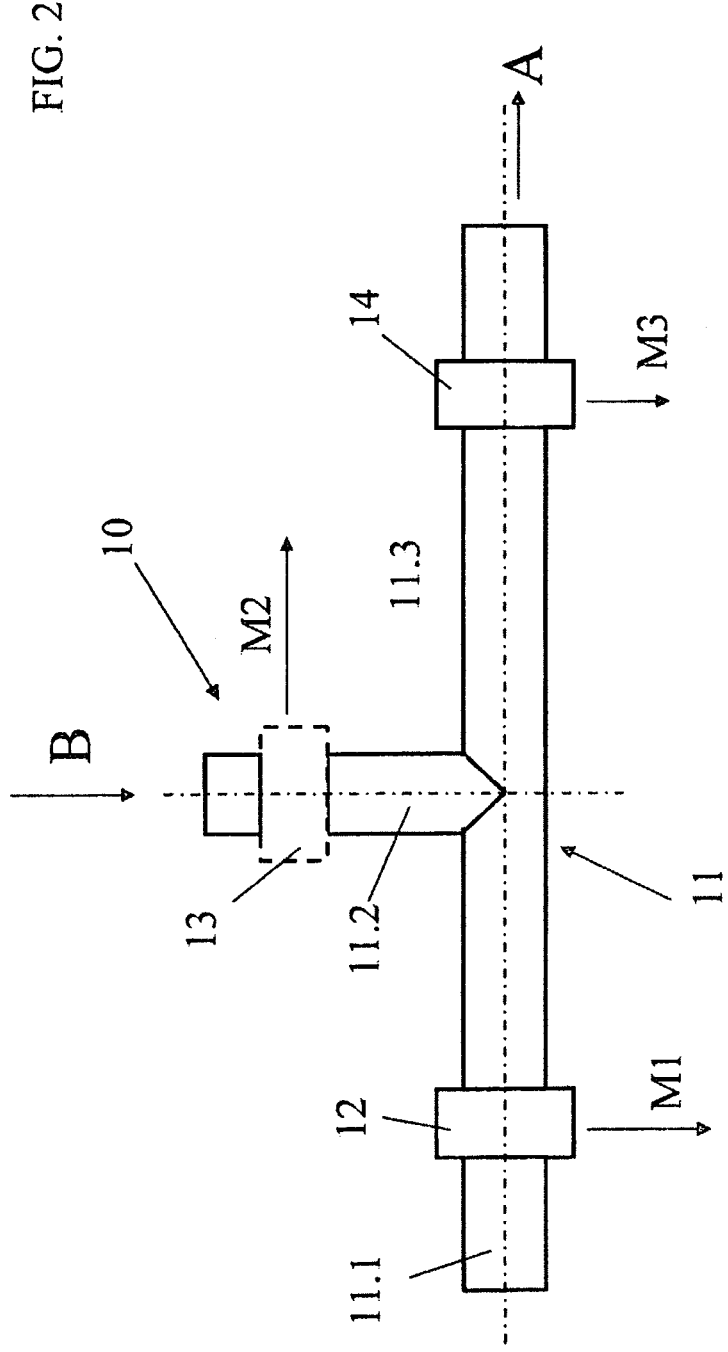
FIG. 2 shows a simplified representation of a measuring device for determining the proportion of filter aid in the unfiltered product supplied to the filter.

The system given the general reference 1 in the Figures is used for filtering a liquid medium or unfiltered product, for example for filtering beverages, including carbonated beverages, e.g. beer. For this purpose, the system 1 is realized with a filter 2, which, in the embodiment represented, is a normally designed filter cartridge, essentially comprising an unfiltered space 5 formed in a tank or a filter housing 3, to which the unfiltered product is supplied at an inlet 5.1, a filtrate space 4 also formed in the filter housing 3 with outlet 4.1 for discharging the filtered medium or filtrate and a plurality of sock-like filter cartridges 6 produced from a material suitable for these types of filter elements and realized open to the filtrate space 4 and with a closed wall to the unfiltered space 5.

In order to obtain the desired filter result, at least one filter aid is added to the unfiltered product, which is supplied via the inlet 5.1, the filter aid being in the form of a suspension containing the filter aid, for example in the form of suspension made from the unfiltered product and the filter aid, or also in the form of a suspension made from water and the filter aid.

Diatomite is particularly suitable as a filter aid; however, the invention is obviously not restricted to the use of this particular filter aid. It is possible to use other suitable filter aids.

In order to obtain the filter result striven for, it is necessary to add a sufficient quantity of filter aid to the medium to be filtered. However, as the maximum quantity of filter aid that can be accommodated by the filter 2 or by the filter cartridge 6, is predetermined, in particular, by the geometric dimensions of the unfiltered product space 4 and of the filter cartridge 6 and by the space between the filter cartridges 6 and, for example, is a maximum of 300 kg and as once this maximum quantity is reached, in each case a cleaning and/or back-flushing of the filter 2 is necessary causing an interruption to the normal production, it is necessary to supply the filter aid or the suspension containing the filter aid in as precisely metered a manner as possible.

This is effected via a metering device 7, which is, for example, a metering pump connected to a device 8 for providing the suspension. The metering device 7 is actuated by a control device 9 as a function of measuring signals or measured values M1-M3, which are determined with a measuring device 10.

The measuring device 10, in the exemplary embodiment represented, comprises, connected upstream of the inlet 4.1, a T-shaped pipe section 11 with three pipe portions 11.1-11.3, of which the pipe portion 11.3 is connected to a line for supplying the unfiltered product, the pipe section 11.2 is connected to the metering device 7 and the pipe portion 11.3 is connected to the inlet 5.1.

The measuring device 10, in the exemplary embodiment represented, also includes three measuring points 12-14, the measuring point 12 at the pipe portion 11.1, the measuring point 13 at the pipe portion 11.2 and the measuring point 14 at the pipe portion 11.3. The measuring points 12-13 are realized such that, in each case, they supply at least one measured value M1-M3, which corresponds to the at least one chemical and/or physical value or a chemical and/or physical characteristic of the liquid medium traversing the respective measuring point 12-14 or flowing past the measuring point, a chemical and/or physical characteristic that, among other things, is also dependent on the quantity of the filter aid entrained with the liquid product or on the concentration of the filter aid in the liquid medium.

The chemical and/or physical values determined from the measuring points 12-14 and/or their changes can be of the most varied type, for example the electric conductivity and/or capacity and/or density and/or viscosity and/or visual reflection capacity and/or visual transparency and/or absolute pressure and/or back-pressure and/or differential pressure or pressure drop at a flow restrictor provided at the relevant measuring point 12-14 and/or PH value.

The measured value M3 supplied from the measuring point 14 consequently corresponds to the chemical and/or physical characteristic of the unfiltered product or a proportion of the filter aid. The measured value M2 supplied from the measuring point 13 corresponds to the chemical and/or physical characteristics of the suspension containing the filter aid and the measured value supplied from the measuring point 12 corresponds to the physical and/or chemical characteristics of the unfiltered product with the filter aid added in a metered manner.

In the control device 9 or in a computer of the control device, from the measured values M1-M2 having regard to characteristic curves or characteristic data, among other things, stored in a storage means at that location, the actual concentration of the filter aid in the unfiltered product supplied to the inlet 5.1 is determined as an actual value and using a required value also stored in the storage means of the control device 9 and/or set at an input of the control device 9, the metering device is readjusted or reset such that the concentration of the filter aid in the unfiltered product supplied to the inlet 5.1 corresponds as precisely as possible to the required value. This readjusting and resetting is effected, for example, corresponding to a characteristic curve that takes account of the characteristics of the system.

The advantage of using a plurality of measuring points 12-14 is that by comparing and/or by processing the measured values M1-M3 supplied from the measuring points, the differences actually in the chemical and/or physical characteristics of the medium traversing the respective measuring point 12-14 produced by the addition of the filter aid are detected and at the same time, it is also possible, in particular, to eliminate from the measured values such components or proportions that result from changes in the chemical and/or physical characteristics of the liquid medium that are not brought about by the addition of the filter aid.

The filter aid is supplied to the metering device 7 as a suspension, comprising a liquid medium, for example the unfiltered product, in which the filter aid has been slurried to form the suspension, for example by using an agitator.

The measuring device 10 is realized, for example, such that all the measuring points 12-14 in each case supply a measured value M1-M3 for a specific chemical and/or physical characteristic, or in parallel or serially, i.e. chronologically in time, supply a plurality of measured values corresponding to different chemical and/or physical characteristics of the liquid medium traversing the respective measuring point, such that by detecting different chemical and/or physical characteristics, the precision of the measurement and consequently also the precision of the metering of the filter aid can be increased.

In principle, it is possible for all the measuring points 12-14 to supply at least one measuring signal corresponding to the same type of chemical and/or physical characteristic of the medium traversing the measuring points or, however, in each case in one measuring cycle, to supply a plurality of measured values that correspond to the different types of chemical and/or physical characteristics of the liquid medium, however, during each measuring cycle in each case the same chemical and/or physical characteristics being detected as measured values at all the measuring points 12-14.

In principle, it is also possible to realize the measuring points 12-13 such that they supply measured values M1-M3 that correspond to different chemical and/or physical characteristics of the liquid medium, the different measured values then being processed in the control device 9 having regard to characteristic data stored at that location.

In a very schematic manner, FIG. 3 shows a time development of one of the measured values M1-M3. As shown in FIG. 3, the respective measured value has a maximum value $M_{max}$ and a minimum value $M_{min}$. This results in each measured value being loaded with certain errors. The true value $M_{actual}$ of the measured variable, as a rule, is between $M_{max}$ and $M_{min}$. The difference between $M_{max}$ and $M_{min}$ depends on the most varied of factors. For example, the difference can depend on errors in the measuring method, on the variables to be measured, on the type of liquid medium to be measured, on the temperature, on the time available for the measuring process, on the carbonated content of the liquid medium, on the proportion of out-gassed CO2, i.e. no longer dissolved in the liquid medium, etc.

In order to obtain as precise a metering as possible, the control device 9 is consequently realized in a preferred manner such that, in each case, the actual measured value $M_{actual}$ is formed from the incoming measured values corresponding to one and the same type of chemical and/or physical characteristic, by storing the incoming measured values M1-M3 and by calculating the value $M_{actual}$ by forming the mean value or by carrying out another suitable algorithm.

The unfiltered product traverses the pipe section 11 in the direction of the arrow A. The suspension containing the filter aid is supplied to the pipe portion 11.2 in the direction of the arrow B.

The invention has been described above by way of one exemplary embodiment. It is obvious that changes and conversions are possible without in any way departing from the inventive concept underlying the invention.

| List of references | |
|---|---|
| 1 | System |
| 2 | Filter |
| 3 | Filter housing |
| 4 | Filtered product space |
| 5 | Unfiltered product space |
| 5.1 | Inlet |
| 6 | Filter cartridge |
| 7 | Metering device |
| 8 | Source for suspension |
| 9 | Control device |
| 10 | Measuring device |
| 11 | Pipe section |
| 11.1-11.3 | Pipe portion |
| 12, 13, 14 | Measuring points |
| M1, M2, M3 | Measured value |
| $M_{max}$ | Maximum value |
| $M_{min}$ | Minimum value |
| $M_{actual}$ | Actual value |
| A | Direction of flow of the unfiltered product |
| B | Direction of supplying the suspension |

The invention claimed is:

1. A method for determining a quantity of filter aid that has been added to a liquid medium in a system that is traversed by said liquid medium and into which filter aid is added, said method comprising, at a first measurement point, obtaining a first measurement of a characteristic, at a second measurement point, obtaining a second measurement of a characteristic, wherein said first measurement point is upstream of where filter aid is added to said system, wherein said second measuring point is downstream of where filter aid is added to said liquid medium, wherein said characteristic is one that changes with concentration of filter aid, wherein said characteristic is selected from the group consisting of physical characteristics and chemical characteristics, whereby, as a result of addition of said filter aid between said first measuring point and said second measuring point, said first measurement differs from said second measurement, and determining an actual quantity of filter aid that has been added to said medium based at least in part on said first measurement and said second measurement.

2. The method of claim 1, further comprising obtaining said first and second measurements at the same time.

3. The method of claim 1, further comprising obtaining said first and second measurements at different times.

4. The method of claim 1, further comprising adding filter aid in a manner that depends on said first and second measurements.

5. The method of claim 1, further comprising, at a third measuring point, obtaining a measurement that corresponds to said characteristics of said suspension containing said filter aid.

6. The method of claim 1, wherein determining an actual quantity comprises retrieving characteristic data associating measured values of said characteristic with an actual value of concentration of filter aid.

7. The method of claim 6, further comprising determining said actual quantity of said filter aid based at least in part on said characteristic data.

8. The method of claim 1, wherein determining an actual quantity comprises eliminating, from said measured values, changes that are not brought about by addition of filter aid.

9. The method of claim 1, wherein determining an actual quantity comprises calculating an actual quantity by applying an algorithm to said measured values.

10. An apparatus for determining a quantity of a filter aid that has been added to a liquid medium, said apparatus comprising a channel, a connection, a first measuring point, a second measuring point, a measuring device, and a control device, wherein said channel is traversable by said liquid medium, wherein said connection is a connection in said channel through which filter aid is added to said liquid medium, thereby forming a suspension, wherein said first measuring point is located upstream of said connection, wherein said second measuring point is located downstream of said connection, wherein said measuring device is configured for obtaining a first measurement and a second measurement, wherein said first measurement is a measurement of a value of a characteristic of said liquid medium at said first measuring point, wherein said second measurement is a measurement of a value of a characteristic of said suspension at said second measuring point, wherein said characteristic is a characteristic that changes in response to addition of filter aid and that is selected from the group consisting of a physical characteristic and a chemical characteristic, and wherein said control device is configured for receiving said first and second measurements and calculating therefrom an actual value of a quantity of filter aid that has been added to said liquid medium.

11. The apparatus of claim 10, further comprising data storage in which is stored characteristic data, said characteristic data that associates measurements of said characteristic with actual concentration.

12. The apparatus of claim 10, wherein said control device is configured to retrieve said characteristic data from said data storage and to determine said quantity of filter aid that has been added based at least in part on said characteristic data.

13. The apparatus of claim 10, wherein said measurement device is configured for obtaining said measurements in parallel.

14. The apparatus of claim 10, wherein said measurement device is configured for obtaining said measurements serially.

15. The apparatus of claim 10, further comprising a detector system for serial acquisition of measured values corresponding to different characteristics of said liquid medium at said measuring points.

16. The apparatus of claim 10, wherein said liquid medium is an unfiltered product to be filtered.

17. The apparatus of claim 10, further comprising means for introducing said filter aid, said means being configured to introduce said filter aid in a manner that depends on said measured values, said manner being selected from said group consisting of a regulated manner and a controlled manner.

18. The apparatus of claim 10, further comprising means for adding up said quantity of said filter aid determined using a measuring method that includes, before addition of said filter aid, measuring a characteristic of said medium that changes by said addition of said filter aid at a first measuring point, after addition of said filter aid, measuring said characteristic at a second measuring point, and determining said quantity of said added filter aid based at least in part on a measured value at said first measuring point and a measured value at said second measuring point, said measured values corresponding to characteristics at said first and second measuring points respectively.

19. The apparatus of claim 10, wherein said channel includes at least three portions and wherein one measuring point is provided on each portion.

20. The apparatus of claim 10, wherein at least one measuring point is realized for parallel acquisition of measured values corresponding to different characteristics of said liquid medium.

21. The apparatus of claim 10, wherein said liquid medium is a suspension containing said filter aid.

* * * * *